United States Patent
Joos et al.

(10) Patent No.: US 10,361,072 B2
(45) Date of Patent: Jul. 23, 2019

(54) ONLINE MASS SPECTROMETER FOR REAL-TIME DETECTION OF VOLATILE COMPONENTS FROM THE GAS AND LIQUID PHASE FOR PROCESS ANALYSIS

(71) Applicant: FRAUNHOFER-GESELLSCHAFT ZUR FÖRDERUNG DER ANGEWANDTEN FORSCHUNG E.V., Munich (DE)

(72) Inventors: Martin Joos, Karlsruhe (DE); Matthias Stier, Schwäbisch Gmünd (DE); Stephan Scherle, Winnenden (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/568,627

(22) PCT Filed: May 4, 2016

(86) PCT No.: PCT/EP2016/060055
§ 371 (c)(1),
(2) Date: Oct. 23, 2017

(87) PCT Pub. No.: WO2016/177810
PCT Pub. Date: Nov. 10, 2016

(65) Prior Publication Data
US 2018/0151341 A1 May 31, 2018

(30) Foreign Application Priority Data

May 5, 2015 (DE) .................. 10 2015 208 250

(51) Int. Cl.
*H01J 49/04* (2006.01)
*G01N 33/18* (2006.01)

(52) U.S. Cl.
CPC ...... *H01J 49/0422* (2013.01); *G01N 33/1826* (2013.01); *H01J 49/0431* (2013.01); *H01J 49/0495* (2013.01)

(58) Field of Classification Search
CPC .. H01J 49/00; H01J 49/02; H01J 49/04; H01J 49/0404; H01J 49/0409; H01J 49/0413;
(Continued)

(56) References Cited

U.S. PATENT DOCUMENTS

| 4,814,612 A * | 3/1989 | Vestal | G01N 30/7253 250/282 |
| 5,324,938 A * | 6/1994 | Hambitzer | G01N 33/0049 250/282 |

(Continued)

FOREIGN PATENT DOCUMENTS

| DE | 4133300 A1 | 4/1993 |
| GB | 2392114 A | 2/2004 |

(Continued)

OTHER PUBLICATIONS

International Search Report for PCT/EP2016/060055, ISA/EP, Rijswijk, NL, dated Aug. 11, 2016, in English and German.
(Continued)

*Primary Examiner* — Jason L McCormack
(74) *Attorney, Agent, or Firm* — Stephen T. Olson; Harness, Dickey & Pierce, P.L.C.

(57) ABSTRACT

The present disclosure relates to a method for analysis by mass spectrometer of liquid and/or gaseous samples, and to an apparatus for carrying out said method. A mass spectrometer is used which has a first flow element for liquid samples and a second flow element for gaseous samples.

9 Claims, 6 Drawing Sheets

Figure 1:
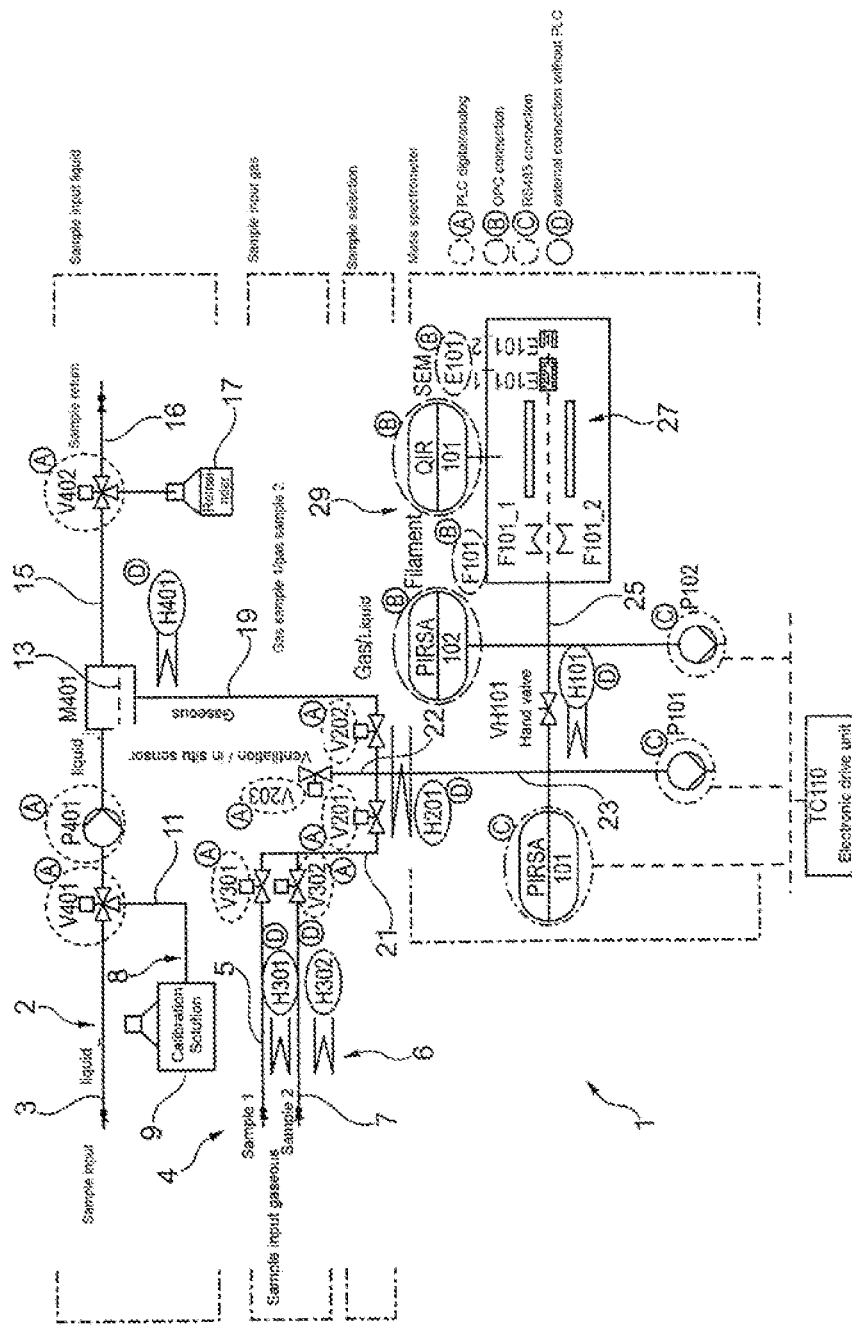

(58) Field of Classification Search
CPC .. H01J 49/0422; H01J 49/0431; H01J 49/044; H01J 49/0445; H01J 49/045
USPC .................................. 250/281, 282, 285, 288
See application file for complete search history.

(56) References Cited

U.S. PATENT DOCUMENTS

| | | | | |
|---|---|---|---|---|
| 5,448,062 | A * | 9/1995 | Cooks | H01J 49/0436 250/288 |
| 6,630,664 | B1 * | 10/2003 | Syage | H01J 49/107 250/288 |
| 2005/0236565 | A1 | 10/2005 | Oser et al. | |
| 2006/0243901 | A1 * | 11/2006 | Barket, Jr. | H01J 49/0031 250/288 |
| 2006/0255261 | A1 * | 11/2006 | Whitehouse | H01J 49/0431 250/288 |
| 2008/0048107 | A1 | 2/2008 | Mcewen | |
| 2009/0294660 | A1 * | 12/2009 | Whitehouse | H01J 49/045 250/288 |
| 2010/0078553 | A1 * | 4/2010 | Corso | H01J 49/062 250/288 |
| 2011/0253889 | A1 * | 10/2011 | Ishimaru | H01J 49/145 250/282 |
| 2011/0266430 | A1 * | 11/2011 | Josland | H01J 49/0431 250/282 |
| 2012/0018632 | A1 | 1/2012 | Whitehouse et al. | |
| 2013/0048851 | A1 * | 2/2013 | Kumano | H01J 49/0431 250/282 |
| 2013/0341503 | A1 | 12/2013 | Whitehouse et al. | |
| 2014/0374589 | A1 * | 12/2014 | Javaheri | H01J 49/062 250/282 |
| 2015/0380226 | A1 * | 12/2015 | Fukui | H01J 49/0445 250/423 R |

FOREIGN PATENT DOCUMENTS

| | | |
|---|---|---|
| WO | WO-2009/146396 A1 | 12/2009 |
| WO | WO-2014/209474 A1 | 12/2014 |

OTHER PUBLICATIONS

Written Opinion of the ISA for PCT/EP2016/060055, ISA/EP, Rijswijk, NL, dated Aug. 11, 2016, in German.
Anonymus: "Foto der Einlass-Systeme des Spektrometers Finnigan MAT95", Apr. 21, 2011 (Apr. 21, 2011), XP055284920, Retrieved from the Internet: URL:https://web.archive.org/web/20110421104620/ http://www.chemgapedia.de/vsengine/vlu/vsc/de/ch/3/anc/masse/ms_einlass_vakuum.vlu/Page/vsc/de/ch/3/anc/masse/2_massenspektrometer/ 2_1_einlasssystem/anschaul/foto_alle_m39ht0402.vscml.html [retrieved on Jun. 30, 2016] the whole document (with machine translation).

* cited by examiner

ONLINE MASS SPECTROMETER FOR REAL-TIME DETECTION OF VOLATILE COMPONENTS FROM THE GAS AND LIQUID PHASE FOR PROCESS ANALYSIS

CROSSREFERENCE TO RELATED APPLICATIONS

This application is a 371 U.S. National Stage of International Application No. PCT/EP2016/060055, filed May 4, 2016, which claims the benefit of and priority to German Patent Application No. 10 2015 208 250.4, filed May 5, 2015. The entire disclosures of the above applications are incorporated herein by reference.

The present invention relates to a method for analysis by mass spectrometer of substances present in liquid and/or gaseous samples, as well as to an apparatus for carrying out said method.

Process mass spectrometers for analysis of a gas phase are known from the state of the art, for example from Thermo Scientific and Extrel CMS, LLC.

Furthermore, DE 41 33 300 A1 discloses an "online" mass spectrometer having a membrane with membrane inlet, with which spectrometer volatile components of an aqueous solution can be detected at a sensitivity in the lower ppb range (ppb="parts per billion," in other words one-billionth). According to the method disclosed in DE 41 33 300 A1, the liquid phase can be continuously passed into a membrane inlet by means of a low-pulsation pump, by way of a capillary, moved past a PTFE membrane in the interior, and either passed back to the starting point by way of a further capillary, or discarded. A pre-vacuum is applied on the permeate side of the membrane inlet, thereby causing the liquid to be continuously evaporated at the membrane surface. If a rotary valve is opened, part of the gas stream situated in the pre-vacuum, also referred to as a fine vacuum, gets into a high vacuum and is measured in the mass spectrometer there, as an ion stream.

However, no mass spectrometer is known from the state of the art with which measurements can simultaneously be taken online, in other words in real time, both from a gas phase and from a liquid, and which can furthermore be operated in reliable manner in a process, and in automated manner.

In summary, it can be said that there is a great need for an apparatus for analysis by mass spectrometer of substances, with which both gaseous and liquid samples can be analyzed without conversion of this apparatus, in automated manner, particularly for process observation.

It is therefore the task of the present invention, in particular, to overcome the aforementioned disadvantages and, in particular, to be able to analyze and determine a method and an apparatus for carrying out an analysis by mass spectrometer of substances present in liquid and/or gaseous samples, preferably in real time and in fully automated manner [sic—incorrect syntax in the German text]. In particular, the present method and the present apparatus are supposed to be characterized in that the apparatus is installed into a reaction system once, and then analyzes the gaseous and/or liquid samples that are present in the reaction system and can be passed to the apparatus, in real time, with a utilization rate of preferably at least 90%, preferably at least 95%, in fully automated manner, and determines the volatile substances contained in them, and, if errors or problems occur, recognizes these on its own, preferably with software support or computer support, and, if necessary, takes suitable corrective measures against them. In particular, the invention is therefore based on the task of creating a method and/or an apparatus for determining volatile substance or substances present in the gaseous state, which also permit continuous determination of these substances, particularly from flowing liquids, in real time, so that regulation procedures with regard to the concentration of specific substances in a liquid and/or a gas mixture can be undertaken, for example in the chemical industry.

This task is accomplished in that the objects of the independent claims are made available. Advantageous embodiments are evident from the dependent claims.

The present invention particularly relates to a method for analysis by mass spectrometer of substances present in liquid and gaseous samples, comprising the steps:

a) optional, preferably valve-controlled introduction of at least one or more substances of a liquid, preferably an aqueous sample, into a first flow element of an apparatus, or of at least one or more substances of a gaseous sample into a second flow element of the apparatus, wherein the first flow element is different from the second flow element, so that the at least one substance or the multiple substances is/are present at least in part, preferably entirely, in the gaseous state, and b) analysis by mass spectrometer of the at least one substance or of the multiple substances present in the gaseous state in step a).

By means of the preferably valve-controlled introduction of the at least one substance of the liquid sample into a first flow element, and the introduction of the at least one substance of the gaseous sample into a second flow element, preferably with time offset, it is advantageously possible to analyze or determine at least one or more substances from both liquid and gaseous samples by mass spectrometer, using a single apparatus. By means of the introduction of the at least one substance of the gaseous sample and of the liquid sample by means of two different flow elements into one and the same apparatus, the result is advantageously achieved that conversion of the apparatus is no longer necessary if the samples to be measured have different aggregate states. As a result, substances from gaseous and liquid samples can be "simultaneously" analyzed or determined, in simple manner. In particular, these substances can be continuously analyzed or determined over a long period of time, with time offset, it is true, but without conversion of the apparatus for analysis by mass spectrometer.

In particular, the method according to the invention can be carried out in automated manner.

According to the invention, it is therefore particularly provided that at least one substance from a liquid sample is introduced into a first flow element, and at least one substance of a gaseous sample is introduced into a second flow element of the apparatus used according to the invention, in other words into two different flow elements, therefore not the same flow element. In particular, the first flow element is different from the second flow element in that the first flow element is provided for introducing at least one substance from a liquid sample, and the second flow element is provided for introducing at least one substance from a gaseous sample.

The invention preferably provides an aforementioned method according to which, in step a) optionally, particularly in valve-controlled manner, at least one or more substances of a liquid sample is/are introduced into a first flow element of an apparatus for analysis by mass spectrometer of substances present in liquid and gaseous samples, or/and at least one or more substances of a gaseous sample is/are introduced into a second flow element of this apparatus, which is different from the first flow element, and wherein this happens in such a manner that after introduction of the at least one or more substances into the first and/or second flow element, the at least one or more substances is/are present in the first and/or second flow element, in each instance, at least in part, preferably entirely in the gaseous state.

The invention preferably makes available a method for analysis by mass spectrometer, using an apparatus for analysis by mass spectrometer of substances present in liquid and gaseous samples, wherein, preferably optionally, particularly in valve-controlled manner, in step a) the at least one or more substances from a liquid, preferably an aqueous sample is/are volatilized, in other words converted to the gaseous state, and subsequently is/are introduced into a first flow element of the apparatus, in part, preferably entirely in the gaseous state, in other words volatilized, or/and wherein at least one or more substances from the gaseous sample is/are introduced into a second flow element of the apparatus, different from the first flow element, so that after introduction of the at least one or more substances into the first and/or second flow element, the at least one or more substances is/are present in the respective flow element, at least in part, preferably entirely in the gaseous state.

In a particularly preferred embodiment, a method for analysis by mass spectrometer of substances present in volatile and gaseous samples is made available, wherein in step a) not only at least one or more substances of a liquid sample is/are introduced into a first flow element of the apparatus used, but also at least one or more substances of a gaseous sample is/are introduced into a second flow element of the apparatus, particularly introduced with time offset, so that after introduction, preferably after introduction with time offset, of the at least one or more substances into the first and second flow element, the at least one or more substances is/are present in the respective flow element, at least in part, preferably entirely in the gaseous state, preferably present with time offset.

The invention particularly provides, in a method step b), for analyzing the at least one substance coming from the liquid sample and the at least one substance coming from the gaseous sample separately from one another, by mass spectrometer.

In a reaction system that contains at least one substance to be analyzed, in a liquid and gaseous phase, it is advantageous that the content of the substances that can be converted to the volatile form, for example the total content of the substance to be analyzed, can be determined in the reaction system to be measured, composed of the liquid and the gaseous phase, by means of introduction, with time offset, of at least one substance from a liquid sample and at least one substance from a gaseous sample of the reaction system.

The method according to the invention is preferably carried out by means of an apparatus according to the invention, wherein this apparatus according to the invention is an apparatus for analysis by mass spectrometer of substances present in liquid and gaseous samples, having at least aa) a mass spectrometer, bb) at least one inlet for a liquid sample, and cc) at least one inlet for a gaseous sample.

Preferably, according to the invention, the at least one inlet for introduction of at least one substance of a liquid sample is an element that precedes the first flow element on the sample side.

Preferably, according to the invention, the at least one inlet for introduction of at least one substance of a gaseous sample is an element that precedes the second flow element on the sample side.

According to the invention, it is preferably provided that the at least one substance to be analyzed in the liquid sample is volatilized in or on a membrane device that is present in the inlet for the liquid sample. In a particularly preferred embodiment, the at least one inlet for the liquid sample can be structured as an in situ sensor that has a membrane. The membrane device can also be configured as a membrane device past which the liquid sample is conducted.

In a particularly preferred embodiment, the present invention makes available a method for analysis by mass spectrometer of substances present in a reaction system, comprising a liquid and a gaseous phase, comprising the steps:
a) optional, preferably valve-controlled introduction of at least one substance of a liquid sample of the reaction system into a first flow element of an apparatus and/or at least one substance of a gaseous sample of the reaction system into a second flow element of the apparatus, wherein the first flow element is different from the second flow element, so that the at least one substance is present in the gaseous state in the first and second flow element, and
b) analysis by mass spectrometer of the at least one substance present in the gaseous state in step a).

In a particularly preferred embodiment, when the method according to the invention is carried out, in step a) not only is at least one substance of a liquid sample introduced into the apparatus, into a first flow element, but also, preferably with time offset, at least one substance of a gaseous sample is introduced into a second flow element, so that, preferably with time offset, the at least one substance is present in the gaseous state in both flow elements, in each instance.

A method according to the invention makes it possible to determine, for example, the total amount of at least one volatile substance both in the liquid and in the gaseous phase, in a reaction system having a gaseous phase and a liquid phase, particularly a closed reaction system, by means of a single apparatus, namely the apparatus according to the invention, using a simple and efficient method. The method of procedure according to the invention makes it possible to provide partial or complete metabolic balances in the most varied reaction systems, particularly for the most varied reactions, particularly biotechnological reactions.

The present invention furthermore provides a method, in a preferred embodiment, wherein in addition, substances or substance components present in non-volatile form are determined by means of a detector for determining non-volatile substances in a liquid phase, which detector is optionally present in the apparatus according to the invention.

In a particularly preferred embodiment, a method as stated above, having the steps a) and b) is made available, wherein in particular, the method steps a), a1), a2), as well as b), particularly i), ii), iii) and iv), described below, are carried out.

The present invention preferably relates to a method wherein in a step a1), which lies ahead of step b), the at least one or more substances present in the gaseous state are introduced into a third flow element of the apparatus, wherein a pressure from 0.01 to 0.5 mbar, preferably 0.15 to 0.2 mbar, is present in the third flow element. Preferably, the at least one or more substances present in the gaseous state, from the gaseous sample, are introduced into a first third flow element, and the at least one or more substances present in the gaseous state from the liquid sample are introduced into a second third flow element, wherein a pressure from 0.01 to 0.5 mbar, preferably 0.15 to 0.2 mbar is present in the first and/or second third flow element. Alternatively preferably, the at least one or more substances present in the gaseous state, from the gaseous sample and the liquid sample, are introduced into the same third flow element, particularly with time offset and separately from one another.

The present invention preferably relates to a method wherein in step a2) that lies ahead of step b), the at least one or more substances present in the gaseous state are introduced into a fourth flow element of the apparatus, wherein a pressure of $10^{-5}$ mbar or less, preferably $10^{-6}$ mbar or less, preferably $10^{-7}$ mbar or less, preferably $10^{-5}$ mbar to $10^{-10}$ mbar, is present in the fourth flow element.

Preferably, the at least one or more substances present in the gaseous state are first introduced into the third and subsequently into the fourth flow element. Preferably, the at least one or more substances present in the gaseous state, of the gaseous sample, are first introduced into a first third flow element and subsequently into a first fourth flow element. Preferably, the at least one or more substances present in the gaseous state, of the liquid sample, are first introduced into a second third flow element and subsequently into a second fourth flow element. Alternatively preferably, the at least one or more substances present in the gaseous state, in the first third and the second third flow element, are introduced into the same fourth flow element. Preferably, a pressure of $10^{-5}$ mbar or less, preferably $10^{-6}$ mbar or less, preferably $10^{-7}$ mbar or less, preferably $10^{-5}$ mbar to $10^{-10}$ mbar, is present in the first and/or second fourth flow element.

The invention preferably relates to a method wherein the analysis by mass spectrometer according to step b) comprises the following steps:
i) ionization of the at least one or more substances present in the gaseous state,
ii) acceleration of the at least one or more substances ionized in step i),
iii) selection of the at least one or more substances accelerated in step ii), and
iv) detection of the at least one or more substances selected in step iii).

Preferably, the analysis by mass spectrometer according to step b) comprises ionization of the at least one or more substances present in the gaseous state and subsequent detection of the at least one or more ionized substances.

A method is preferred that comprises the following steps:
a) optional, preferably valve-controlled introduction of at least one or more substances of a liquid sample into a first flow element of an apparatus, or at least one or more substances of a gaseous sample into a second flow element of the apparatus, wherein the first flow element is different from the second flow element, so that the at least one or more substances are present at least in part, preferably entirely, in the gaseous state,
a1) at least partial, preferably partial or complete introduction of the at least one or more substances present in the gaseous state, in the first and/or second flow element into a third flow element of the apparatus, wherein a pressure of 0.01 to 0.5 mbar, preferably 0.15 to 0.20 mbar, is present in the third flow element,
a2) at least partial, preferably partial or complete introduction of the at least one or more substances present in the gaseous state, in the third flow element, into a fourth flow element of the apparatus, wherein a pressure of $10^{-5}$ mbar or less, preferably $10^{-6}$ mbar or less, preferably $10^{-7}$ mbar or less, preferably $10^{-5}$ mbar to $10^{-10}$ mbar is present in the fourth flow element, and
b) at least partial, preferably partial or complete analysis by mass spectrometer of the at least one or more substances present in the gaseous state, in the fourth flow element, wherein analysis by mass spectrometer preferably comprises the following steps:
i) at least partial, preferably partial or complete ionization of the at least one or more substances present in the gaseous state, in the fourth flow element,
ii) at least partial, preferably partial or complete acceleration of the at least one or more substances ionized in step i),
iii) at least partial, preferably partial or complete selection of the at least one or more substances accelerated in step ii), and
iv) at least partial, preferably partial or complete detection of the at least one or more substances selected in step iii).

Preferably, the first, the second, the third, preferably the first and/or second third, and/or the fourth, preferably the first and/or second fourth flow element is/are a line, preferably a pipe or a hose, preferably a metal pipe or metal corrugated hose, preferably a stainless-steel pipe or stainless steel corrugated hose.

In a particularly preferred embodiment, the first, the second, the third, and the fourth flow element, particularly the first and the second flow element can be structured to have the same construction.

The method according to the invention and the apparatus according to the invention can particularly advantageously be used for quantitative and qualitative determination of volatile substances in a reaction system, which reaction system is composed of a liquid and a gaseous phase, particularly has a liquid and a gas or a gas mixture. The method according to the invention and the apparatus according to the invention make it possible to determine the volatile substances simultaneously or with time offset, both in the liquid and in the gaseous phase of such a reaction system, so that advantageously, educt and product concentrations, for example, can be detected in reaction systems, in which aggregate state changes occur within the scope of one or more biochemical reactions. In this way, educt and product concentrations can be detected simultaneously or almost simultaneously, in order to thereby obtain the most precise picture possible of a reaction that is present at a specific point in time, without any or without any great time offset between measurement of the educt and of the product. This makes direct detection and monitoring of the respective reaction possible. The method of procedure and the apparatus according to the invention make such a method of procedure possible by means of a single apparatus and a method carried out using it.

The present invention therefore also makes available methods for analysis by mass spectrometer of substances contained in a reaction system composed of at least one liquid and at least one gaseous phase, wherein a method for analysis by mass spectrometer of substances present in liquid and gaseous samples, according to the present invention, particularly comprising the steps a) and b), is carried out, in order to determine the substances, preferably comprising the steps a), a1), and a2) and/or in step b), the steps i), ii), iii), and iv).

In a particularly preferred embodiment, such a reaction system is a bioreactor having at least one liquid reaction medium and at least one gas phase, particularly for fermentation, bio-decomposition of products, conversion of substances or production of substances.

In a particularly preferred embodiment, the concentration not only of the starting materials but also of the end products can be efficiently determined by means of a single apparatus, by means of this method.

In a preferred embodiment, a reaction system having a liquid and a gaseous phase can be used in the sector of biotechnology, the chemical industry, petrochemistry, pharmacy, medical technology, and the foods industry.

In connection with the present connection, the term "and/or" is understood to mean that the members or a group that are connected with one another using the term "and/or" are disclosed alternatively to one another, partly cumulatively or entirely cumulatively. This means, for example for the term "A, B, and/or C," that the following disclosure content should be understood to be meant: A or B or C or (A and B) or (A and C) or (B and C) or (A and B and C).

Preferably, the first, the second, and the third flow element are connected with one another by means of a first valve device, preferably directly. Preferably, the third flow element is connected with the fourth flow element by way of a second valve device, preferably directly. Preferably, the first valve device connects the first flow element with the third flow element in a first position. In a second position, the first valve device connects the second flow element with the third flow element. In a third position, there is no fluid contact between the first and the second flow element as well as the third flow element. Preferably, the second valve device connects the third flow element with the fourth flow element in a first position. In a second position, there is no fluid contact between the third flow element and the fourth flow element.

In an alternative embodiment, the first flow element is connected with the third flow element by means of a first valve device, preferably directly, with one another. In addition, the second flow element is connected with the third flow element by means of a second valve device, preferably directly, with one another. Preferably, the third flow element is connected with the fourth flow element by way of a third valve device, preferably directly. Preferably, the first valve device connects the first flow element with the third flow element in a first position. In a second position, there is no fluid contact between the first and the third flow element. Preferably, the second valve device connects the second flow element with the third flow element in a first position. In a second position, there is no fluid contact between the second and the third flow element. Preferably, the third valve device connects the third flow element with the fourth flow element in a first position. In a second position, there is no fluid contact between the third and the fourth flow element.

In an alternative embodiment, the first flow element is connected with the first third flow element by means of a first valve device, preferably directly, with one another. In addition, the second flow element is connected with the second third flow element by means of a second valve device, preferably directly, with one another. In addition, the first third, the second third, and the fourth flow element are connected with one another by means of a third valve device, preferably directly. Preferably, in this regard the first valve device connects the first flow element with the first third flow element in a first position. In a second position, there is no fluid contact between the first flow element and the first third flow element. Preferably, the second valve device connects the second flow element with the second third flow element in a first position. In a second position, there is no fluid contact between the second flow element and the second third flow element. Preferably, the third valve device connects the first third flow element with the fourth flow element in a first position. Preferably, the third valve device connects the second third flow element with the fourth flow element in a second position. In a third position, there is no fluid contact between the first third flow element, the second third flow element, and the fourth flow element.

In an alternative embodiment, the first flow element is connected with the first third flow element by means of a first valve device, preferably directly, with one another. In addition, the second flow element is connected with the second third flow element by means of a second valve device, preferably directly, with one another. In addition, the first third flow element is connected with the first fourth flow element by means of a third valve device, preferably directly, with one another. In addition, the second third flow element is connected with the second fourth flow element by means of a fourth valve device, preferably directly, with one another. Preferably, in this regard the first valve device connects the first flow element with the first third flow element in a first position. In a second position, there is no fluid contact between the first flow element and the first third flow element. Preferably, the second valve device connects the second flow element with the second third flow element in a first position. In a second position, there is no fluid contact between the second flow element and the second third flow element. Preferably, the third valve device connects the first third flow element with the first fourth flow element in a first position. In a second position, there is no fluid contact between the first third flow element and the first fourth flow element. Preferably, the fourth valve device connects the second third flow element with the second fourth flow element in a first position. In a second position, there is no fluid contact between the second third flow element and the second fourth flow element.

Preferably, each inlet for a gaseous sample or a liquid sample has a third and fourth flow element, wherein the different flow element trains are brought together only directly ahead of the mass spectrometer, by way of a valve device.

Preferably, each inlet for a liquid sample has a first flow element, a third and a fourth flow element assigned to it, and each inlet for a gaseous sample has a second flow element, a third and a fourth flow element assigned to it, wherein the different flow element trains are brought together only directly ahead of the mass spectrometer, by way of a valve device.

By means of the first, second, third and/or fourth valve device, it is particularly possible to control the mass stream of gaseous substances into the third and/or fourth flow element(s), in targeted manner.

Preferably, the first, second, third and/or fourth valve device has at least one, preferably at least two, preferably precisely one, preferably precisely two valves. Preferably, the at least one valve is a switch valve, drum valve or a proportional valve. The at least one valve is preferably configured as an electrical or pneumatic valve.

Preferably, the valves, preferably all the valves, can be controlled, preferably by way of a software-based control program or a memory-programmable controller.

Preferably, a calibration solution is introduced into the first flow element for calibration of the mass spectrometer, instead of a liquid sample. Preferably, a calibration gas or calibration mixture is introduced into the second flow element for calibration of the mass spectrometer, instead of a gaseous sample, preferably in valve-controlled manner.

The present invention preferably relates to a method wherein the first, the second, the third and/or the fourth flow element is/are heated to a temperature of 60 to 80° C., preferably 70 to 75° C. Heating of the flow elements preferably takes place by means of a heating element. Preferably, a heating element is assigned to the first, the second, the third and/or the fourth flow element, in each instance. Preferably, the same temperature is present in the first, the second, the third and/or the fourth flow element.

The term "the third flow element" or "the fourth flow element" comprises one or more flow elements of the same type. Accordingly, these terms also include the first third/fourth and the second third/fourth flow element, if these are present in the apparatus.

By means of heating one or more flow elements, deposition, preferably condensation or absorption of the at least one or more materials or substances present in the gaseous state on the inside of the flow element, preferably of the line, preferably of the pipe or of the hose, preferably of the metal pipe or of the metal corrugated hose, preferably of the stainless-steel pipe or of the stainless steel corrugated hose, is prevented.

In particular, it is prevented, by means of the first, second, third and/or fourth valve device, that an overly large amount of the gaseous or liquid sample and/or of a calibration medium gets into the flow elements, preferably into the third and/or fourth flow element, or into the mass spectrometer. In this way, damage, particularly of the mass spectrometer, is minimized, preferably prevented.

The present invention preferably relates to a method wherein the optional introduction of the at least one or more substances of the liquid or gaseous sample into the first or second flow element is controlled in such a manner that in step a1) and/or a2), the same amounts of the at least one or more gaseous substances are present in the third flow element. According to the invention, the term "equal amounts" is understood to mean that the mass stream from the first flow element into the third flow element and the mass stream from the second flow element into the third flow element differ maximally by ±10%, preferably maximally by ±5%, preferably maximally by ±1%, preferably by way of control of the valve device. Preferably, the term "mass stream" is understood to mean the mass of the at least one or more substances introduced into the third flow element over a specific period of time. By means of this special method management, namely by means of introduction of the same amounts of the at least one or more gaseous substances into the third flow element, it is particularly possible to switch back and forth, in fully automated manner, between the first and the second flow element, in other words between the introduction of the at least one or more substances of a gaseous or of a liquid sample. In particular, it is thereby possible to calibrate the apparatus for analysis by mass spectrometer using a single calibration medium, and subsequently to introduce different samples by way of the first and the second flow element.

Preferably, at least one or more substances of at least two, preferably at least five, preferably at least ten different liquid samples are introduced by way of the first flow element, by way of different inlets, in each instance, preferably with time offset.

Preferably, at least one, preferably at least two, preferably at least five, preferably at least ten, preferably maximally thirty, preferably maximally twenty different substances of a liquid sample are introduced by way of the first flow element.

Preferably, at least one or more substances of at least two, preferably at least five, preferably at least ten different gaseous samples are introduced by way of the second flow element, by way of different inlets, in each instance, preferably with time offset.

Preferably, at least one, preferably at least two, preferably at least five, preferably at least ten, preferably maximally thirty, preferably maximally twenty different substances of a gaseous sample are introduced by way of the second flow element.

The invention preferably relates to a method wherein the pressure in the fourth flow element is detected. Preferably, the pressure in the first, the second, the third and/or the fourth flow element is detected. Preferably, the pressure is detected both in the third and also in the fourth flow element. This detection preferably takes place by means of a detection unit, in each instance. Preferably, this detection unit is connected with a control unit. Preferably, the control unit has a software-based control program or a memory-programmable controller.

The present invention preferably relates to a method wherein a controllable valve device disposed between the third and fourth flow element is closed if a pressure increase is detected in the fourth flow element, so that there is no fluid contact between the third and fourth flow element. Preferably, the controllable valve device disposed between the third and fourth flow element is closed if a pressure increase is detected in the third flow element, so that there is no fluid contact between the third and fourth flow element.

Alternatively or in addition, if a pressure increase is detected in the third flow element, preferably a controllable valve device disposed ahead of the third flow element—in the flow direction of the gaseous substances—is closed. Preferably, if a pressure increase is detected in the and/or fourth flow element, all the valve devices present in the apparatus are closed, so that there is no fluid contact between the flow elements connected using these valve devices, preferably directly. By means of closing the at least one valve, it is preferably prevented that an overly large amount of gaseous substances, but also an overly large amount of a gaseous or liquid sample can penetrate into the measurement device, in other words into the mass spectrometer used to analyze the at least one or more gaseous substances.

Preferably, the at least one or more gaseous substances flow out of the fourth flow element, preferably directly, into the mass spectrometer, in other words into the ionization device of the mass spectrometer that is configured and provided for carrying out the step i).

Preferably, the present method consists of the aforementioned method steps, preferably of the method steps a), a1), a2), b), i), ii), iii), and iv). Preferably, no fractionation of the at least one or more substances present in the gaseous state takes place in step a), before they are analyzed by mass spectrometer in step b). Preferably, the method according to the invention or the method preferred according to the invention is free of chromatographic, particularly gas-chromatographic fractionation, preferably of the at least one or more substances present in the gaseous state.

Preferably, analysis by mass spectrometer of reactions takes place in gases or gas mixtures or liquids.

Preferably, using the present method, ion streams of the one or more gaseous substances are measured, thereby making it possible to calculate the respective concentrations of these substances.

To produce the vacuum that is present in the third and/or fourth flow element, a pump is used, in each instance, which is designed for production of a corresponding pressure, in each instance.

In a preferred embodiment of the present invention, the liquid sample is conducted past a membrane that is not permeable for liquid but is gas-permeable, and present in a membrane device, also referred to as a membrane module, for introduction into the first flow element, in such a manner that under the conditions that prevail during the method, at least one or more substances can be volatilized, in other words brought into the gas phase. Corresponding substances pass through the membrane and are thereby introduced into the first flow element. Preferably, it is provided that the liquid is kept at a constant temperature, preferably at a temperature between 10 to 30° C., preferably 25° C., in the region of the membrane.

Preferably, the temperature can be varied for the respective application. Preferably, the temperature remains constant during the measurement period, preferably the entire measurement period. Preferably, calibration takes place at the same temperature.

Preferably, introduction of the at least one or more substances of the liquid sample into the first flow element and/or introduction of the at least one or more substances of the gaseous sample into the second flow element take(s) place in such a manner that the first flow element or the second flow element is connected with the third flow element fluidically by way of the valve device, preferably directly, in other words a certain suction effect, but also a partial vacuum in the first and/or second flow element occurs as the result of the partial vacuum that is present in the third flow element.

In a preferred embodiment of the present invention, it is provided that the liquid sample moved past the membrane is conducted in the branch or secondary branch of the liquid stream to be examined. In a preferred embodiment, the membrane device is constructed for introduction of volatile substances from a liquid sample, in such a manner that it functions as a bypass, wherein the liquid sample is taken from a container or from a line, by means of a low-pulsation pump, and optionally returned.

The membrane is preferably supported by a porous disk. The membrane is sealed off in a membrane housing by means of a sealing ring sheathed with polytetrafluoroethylene.

To keep the vacuum in the third and/or fourth flow element constant, the vacuum detection apparatuses that are assigned to the third and/or the fourth flow element are connected with the vacuum pumps assigned to these flow elements, by way of control circuits, particularly controlled by way of a control unit.

In a particularly preferred embodiment, a method for analysis by mass spectrometer of substances present in liquid and gaseous samples, according to the method disclosed above, is made available, additionally comprising a step of the determination of non-volatile substances present in a liquid sample. In a particularly preferred embodiment, such determination takes place by means of an apparatus according to the invention, which has a detector for determination of non-volatile substances present in a liquid sample.

The present invention also relates to an apparatus for analysis by mass spectrometer of substances present in liquid and gaseous samples, having aa) a mass spectrometer,
bb) at least one inlet for a liquid sample, and
cc) at least one inlet for a gaseous sample.

Preferably, the at least one inlet for a liquid sample is different from the at least one inlet for a gaseous sample.

The apparatus according to the invention preferably has the flow elements described above, particularly a first flow element that follows the at least one inlet for a liquid sample, and a second flow element that follows the at least one inlet for a gaseous sample, as well as optionally, a third and/or fourth flow element, wherein the first flow element is different from the second flow element.

The present invention preferably relates to an apparatus wherein the apparatus is set up for carrying out a method according to the invention or a method preferred according to the invention.

Preferably, the method according to the invention or the method preferred according to the invention is carried out using an apparatus according to the invention or an apparatus preferred according to the invention.

In particular, the present apparatus according to the invention is characterized in that it is a very compact apparatus, low in dead volume.

The present invention preferably relates to an apparatus wherein the at least one inlet for a liquid sample has a hydrophobic, at least partly porous membrane. This membrane is preferably situated in a membrane device.

The membrane is preferably a hydrophobic membrane. The membrane preferably has a plurality of pores, wherein the average pore radius preferably has a value of 0.001 to 0.1 µm, preferably 0.01 to 0.05 µm. The membrane preferably has a thickness of 1 to 100 µm, preferably 10 to 80 µm, preferably 40 to 60 µm. The membrane preferably has a porosity from 40 to 80%, preferably from 50 to 70%. The membrane is preferably a pervaporation membrane, preferably a polytetrafluorethylene (PTFE) membrane or a silicone membrane, preferably a polydimethylsiloxane (PDMS) membrane, preferably a polytetrafluoroethylene (PTFE) membrane. Alternatively, other specific membranes can also be used, which are selective for specific materials, in order to thereby obtain a better resolution of the measurement, if necessary. Preferably, tight pervaporation membranes, preferably a silicone membrane, preferably a PDMS membrane, are also used as membranes.

Preferably, a PTFE membrane is used as an inlet for at least one substance capable of being volatilized, from a liquid sample, in a fermentation process or cell culture process, particularly as an integral component of a fermentation process container or cell culture process container, preferably of a corresponding disposable container.

The invention preferably relates to an apparatus that additionally has at least one inlet for a calibration medium.

The present invention preferably relates to an apparatus that at least one valve device, which is disposed between the inlets and the mass spectrometer.

Preferably, the at least one valve device is disposed, spatially and/or functionally, between the inlets and the mass spectrometer.

The present invention preferably relates to an apparatus wherein the at least one inlet for a liquid sample is configured as an in situ sensor.

Particularly preferably, the present apparatus has a membrane device configured as an in situ sensor. This in situ sensor particularly serves, in a liquid reaction medium or in a liquid medium, for extracting the substances capable of being volatilized from this medium, so that these substances can be introduced into the first flow element. In particular, this in situ sensor can be used in biotechnology, particularly in the form of an Ingold connector. This is considered to be a standard connector coupling for installation in process containers, particularly in reactors, pipelines and/or other system components.

Preferably, the in situ sensor has a cylindrical inner part having an outside thread, and a sleeve having an inside thread; preferably, it consists of these, wherein the cylindrical inner part is screwed into the sleeve, wherein the inside thread and the outside thread interact. The inner part furthermore has a line that extends in the longitudinal direction, preferably a bore, thereby causing a fluid connection between the liquid medium or sample and the inlet of the apparatus for the liquid samples to exist. In particular, this line is electropolished. By means of this electropolishing, adsorption, in other words condensation of the materials present in the gaseous state, which are fed in through the membrane, on the surface of this line is prevented. Preferably, the in situ sensor has a heating element, so that the entire sensor can be heated and is also heated during use in the method according to the invention or the method preferred according to the invention. The membrane is clamped in place using a suitable gasket, preferably an O-ring gasket, between the inner part and the sleeve, preferably by means of screwing the sleeve in tightly. At this end, the sleeve has an opening, preferably a bore, so that the liquid sample can wet the membrane with a sufficient amount when used as intended. Accordingly, the single possible path that is provided for the fluid, i.e. the liquid sample, into the first flow element, as intended, is by way of the membrane. This membrane is preferably inserted into the in situ sensor in such a manner that a curvature to the outside, in other words in the direction of the liquid or sample, preferably a slight curvature, comes about. By means of this preferred curvature, the contact surface of the membrane with the liquid, which preferably flows past it, is increased in size, so that the volatilization of the volatile substances present in the medium is improved and/or the biofilm formation on the membrane in a fermenter is reduced, particularly due to the better attack surface of the liquid that is preferably flowing past. To prevent biofilm formation, a wiping element is preferably provided alternatively or in addition. Preferably, this membrane is supported by a disk, preferably a sintered disk, preferably counter to the curvature. By means of a cap nut that is also present, the in situ sensor can preferably be attached to a reaction vessel, preferably to a fermenter, and preferably ends flush with the reactor interior, preferably fermenter interior, preferably in liquid-tight manner, preferably in fluid-tight manner, by way of a ring seal that lies against the sleeve on the outside. Preferably, the liquid stream and the pressure at the membrane are taken into consideration in the method according to the invention or the method preferred according to the invention. Alternatively, the in situ sensor can also be configured as a flow sensor, which is preferably installed in a line, preferably in a pipe.

The in situ sensor can also be integrated into a stirrer, a baffle or into the reactor wall of a reaction vessel. The in situ sensor is preferably used as an integral part of a fermentation process container or cell culture process container, preferably of a corresponding disposable container. The in situ sensor for holding the membrane preferably consists of plastic, preferably PTFE, or other materials. The membrane can be composed of the same or a different material.

The present invention preferably relates to an apparatus wherein the at least one inlet is configured for a gaseous sample, as a capillary inlet.

The present invention preferably relates to an apparatus wherein the capillary inlet has a capillary that is coated with quartz and can be heated.

The present invention preferably relates to an apparatus wherein the mass spectrometer has an ion source, an analyzer, and a detector.

The present invention preferably relates to an apparatus wherein the mass spectrometer is a quadrupole mass spectrometer.

The present invention preferably relates to an apparatus wherein the mass spectrometer is a process mass spectrometer.

In a preferred embodiment, the apparatus has a membrane device for volatilization of substances present in a liquid sample, a capillary for the inlet of a gaseous sample, and an in situ sensor for the inlet of a liquid sample; preferably, these components are connected by way of a crosspiece and switchable valves, and can be controlled in automated manner. In a preferred embodiment, the apparatus has at least two membrane devices for volatilization of substances present in a liquid sample, and a capillary for the inlet of a gaseous sample, wherein at least one membrane device is configured as an in situ sensor for the inlet of a liquid sample.

In particular, the apparatus is designed as a transportable and autarchic module. The present apparatus is preferably present in a transportable encapsulation.

Accordingly, the apparatus can be integrated into existing process sequences.

The present apparatus is particularly able to bring different samples, both gaseous and liquid samples, and calibration media, preferably calibration solutions, to analysis by mass spectrometer or determination of substances present in the gaseous state, without conversion of the apparatus.

Preferably, the apparatus also has an inlet for an acid or a base. By means of adding an acid or a base, the sensitivity of the mass spectrometer for specific materials is increased, in that depending on the $pK_S$ value of the substance to be measured, its volatility is improved by means of protonation or deprotonation. In particular, the acid or base is first introduced into the liquid sample by means of a pump, particularly if the membrane device is mounted in a bypass. In particular, introduction of an acid or base in the bypass can be made possible by means of using two low-pulsation pumps.

By means of the present apparatus, analysis by mass spectrometer or determination of correspondingly volatile substances can be carried out without conversion measures, alternately both from a liquid sample and from a gaseous sample. By means of at least one releasable flow element connection, also referred to as a flange, which has a valve device, one or more further inlets for gaseous and/or liquid samples can be made available.

The present apparatus preferably has at least one heating element per flow element that is present. By means of these heating elements, a uniform temperature profile can particularly be ensured, in order to thereby prevent adsorption or condensation of the gaseous substances on the inner side of the flow elements, particularly the line.

Preferably, all the flow elements and valve devices, particularly all the surfaces with which the substances present in the gaseous state can come into contact, are electropolished. Adsorption or condensation of the substances present in the gaseous state is also prevented by means of the electropolishing.

The apparatus according to the invention or the apparatus preferred according to the invention particularly has a control system. By means of the control system, communication with the mass spectrometer, the valve devices, particularly the valves, and the installed pumps is possible. As a result, the apparatus can be used in autarchic manner, in a broad application field.

The control system of the apparatus preferred according to the invention particularly makes it possible to control the method according to the invention in such a manner that with time offset, at least one substance from a liquid sample and at least one substance from a gaseous sample, particularly from a reaction system containing a liquid and a gaseous phase, are withdrawn and, one after the other, in the gaseous state, passed to analysis by mass spectrometer of the substances to be analyzed.

The ion streams measured in the mass spectrometer, preferably with other process parameters, are preferably transferred to the control system. In this way, a pressure drop or pressure increase can be detected and therefore registered, and therefore if failure is suspected, for example penetration of liquid, part or all the valves in the apparatus, particularly of the inlets can be closed.

Preferably, mathematical models are stored in the memory of the control system, and thereby ion streams are converted to concentrations on the basis of automated calibration. The required parameters for carrying out the method, such as the educts used and the products to be expected, can be queried on the user interface of the control system. The control system preferably has an automated calibration program. Specific method sequences can be programmed with the control system. In particular, the intervals between measurement of a gaseous sample, of a liquid sample or of a calibration medium can be established, particularly by way of control of the different valves.

In particular, at least one interface is also integrated into the apparatus, thereby making it possible to transmit the mass spectrometry values measured in the present case to overriding control systems, particularly reactor control systems. Also, it is possible to transmit measurement values measured by other measurement apparatuses, particularly the pH value, oxygen partial pressure and carbon dioxide partial pressure, conductivity, amount of substances added, and optical density in a reaction medium, by means of corresponding interfaces. The apparatus according to the invention therefore particularly comprises a control system, which has interfaces for further devices, for example for recording operating parameters, and for values received from further measurement apparatuses, for example for preferably qualitative and/or quantitative determination of non-volatile substances in the liquid sample or for detectors for determination of the pH value, of oxygen partial pressure and carbon dioxide partial pressure, conductivity, amount of substances added and/or optical density.

The control system used according to the invention is characterized by a compact structure. The control system preferably has interfaces for input and output of measurement values as well as process parameters, interfaces to data memories, interfaces that allow remote access, including a maintenance mode and a maintenance service, interfaces to process control systems, particularly for determination of control values with inclusion of further data of the process control system, interfaces to a calibration module, or has an integrated calibration module, particularly for automatic calibration of the components to be measured, with control of valves, pumps, and sensors, particularly with regard to valve positions for the status of the calibration solution and the temperature, as well as at least one communication device to the mass spectrometer itself, the pumps used, particularly high-vacuum pumps and pre-vacuum pumps, as well as, preferably by way of the valves, to the at least one inlet for a liquid sample and the at least one inlet for a gaseous sample, as well as, if applicable, to further inlets for further gaseous or liquid samples. In a preferred embodiment, the control system has a housing and a display, particularly a touch screen.

Preferably, further measurement values, preferably the living cell count of microorganisms, are estimated, preferably by way of a soft sensor.

The term "soft sensor" (a combination of the words "software" and "sensor"), also referred to as a virtual sensor or sensor fusion, is understood not to mean a real, existing sensor, but rather a dependency simulation of representative measurement variables to arrive at a target variable. Therefore the target variable is not measured directly, but rather calculated using measurement variables that correlate with it and a model of the correlation. Therefore it is possible to draw conclusions regarding the concentration of non-volatile substances on the basis of gaseous and/or substances capable of being volatilized, particularly if the concentration of the non-volatile substance correlates with the concentration of the gaseous substance and/or substance capable of being volatilized, on the basis of a reaction that takes place.

In a particularly preferred embodiment, the apparatus according to the invention, for analysis by mass spectrometer of substances present in liquid and gaseous samples, has aa) a mass spectrometer, bb) at least one inlet for a liquid sample, cc) at least one inlet for a gaseous sample, and, in addition a detector for determination, particularly quantitative and/or qualitative determination, of non-volatile substances present in a liquid sample.

The apparatus according to the invention is thereby preferably able to detect the volatile substances in the liquid and/or gaseous phase of a reaction system by mass spectrometer, on the one hand, and, on the other hand, to determine the non-volatile substances present in the liquid phase of the system by means of the detector for qualitative and/or quantitative detection of these substances.

In a preferred embodiment, the detector is an optical detector, a detector for electromagnetic radiation or an ultrasound detector.

It is advantageous that reactions can be analyzed and recorded with the present apparatus, in real time.

The term "in real time" is understood to mean that the at least one substance that was introduced can be analyzed within seconds, preferably within one second.

Furthermore, it is characterized by great robustness, great specificity, and easy operability, low maintenance effort, low operating costs, and the possibility of integrating the measurement system into existing processes.

Furthermore, it is possible, using the present apparatus, to measure substances even in very low concentrations, both from a liquid and from a gaseous sample, with a time delay short enough to be ignored.

In particular, with regard to industrial biotechnology, there are further advantages. In particular, the product concentration in the case of fermentations can be determined without great effort and precisely, in real time, by means of measuring the products that occur. Accordingly, the fermentation can be optimized with regard to maximal product formation rate, and the space/time yield can be increased by means of real-time measurement of the products and the byproducts. Furthermore, multiple reactors can be connected with the apparatus according to the invention.

In the case of waste gas analysis in bioprocesses, measurement of the partial pressures of $CO_2$ and $O_2$ are frequently measured [sic—incorrect syntax in the German] to be able to draw conclusions regarding cell growth and product formation rate. By means of the structure according to the invention, particularly by means of the method and the apparatus, the entire composition of the waste gas, including the products, can be measured. Furthermore, the gas-dissolved concentration of $CO_2$ and oxygen and all other volatile substances from the fermentation broth can be measured by means of the inlet for the liquid sample.

The apparatus is suitable for measuring the most varied products, and can therefore also be used for different production processes that change in accordance with seasonal raw material availability and/or customer demand. Accordingly, the present apparatus can be implemented as a custom-tailored analysis device integrated into production systems.

Furthermore, in addition to process monitoring, monitoring of product quality is also important. In biotechnology, contaminants in the product come about by way of different metabolic paths. For example, ethanol is contaminated by methanol, acetaldehyde, ethyl acetate, and diacetyl. These contaminants can be detected with the present apparatus. It can therefore be used as an analysis device for detection of contaminants caused by volatile substances, in other words for quality control. The apparatus according to the invention can therefore preferably be used in beer production.

The present apparatus can be used in the sector of research and development, process monitoring of all types of process media with volatile components, up to quality control, for example in the branches of the chemical industry, petrochemistry, biotechnology, pharmacy, medical technology, and foods industry. It can be used in laboratory systems and/or pilot plants, production locations, particularly for optimization of the production processes that take place there. It can also be used in production in modular and flexible systems.

Because of the possibility of also detecting trace substances with the present apparatus, this apparatus is also suitable for quality assurance in sensitive production sectors, as well as for monitoring of drinking water and/or waste water. In particular, it is possible, using the present apparatus, to measure all the volatile components of liquid, preferably aqueous samples, and also gaseous samples, and, in this regard, to be able to record concentration changes over eight powers of ten, from the low ppb range up to the range of high powers. Furthermore, the apparatus has low response times and the possibility of measuring up to 30, preferably 20 substances at the same time.

In particular, the present apparatus can be used in industrial biotechnology and in bio-based production, as a measurement device for process analysis. In particular, the apparatus can be used in enzymatic processes, for example in the production of butane diol, propane diol, succinic acid, ethanol from lignocellulose, butanol, polyols, acryl acid butyl esters, thiols, esters, lactic acid.

Likewise, the apparatus can be used in medical technology, for example in order to be able to measure the gas composition of respiratory air, the gas emission of the skin, and all volatile components directly from the blood.

The description of the method for analysis by mass spectrometer, also referred to in brief as analysis method, and the description of the apparatus for analysis by mass spectrometer, also referred to in brief as analysis apparatus, should be understood to be complementary to one another. Method steps of the analysis method, which were explicitly or implicitly described in connection with the analysis apparatus, are preferably individual steps or steps combined with one another, of a preferred embodiment of the analysis method. Characteristics of the analysis apparatus, which were described explicitly or implicitly in connection with the analysis method, are preferably individual characteristics or characteristics combined with one another of a preferred exemplary embodiment of the analysis apparatus. This apparatus is preferably characterized by at least one characteristic that is contingent upon at least one step of a preferred embodiment of the analysis method. The analysis method is preferably characterized by means of at least one method step that is contingent upon at least on characteristic of the analysis apparatus.

In the following, the invention will be explained in greater detail, using the following five drawings.

Figure 2:
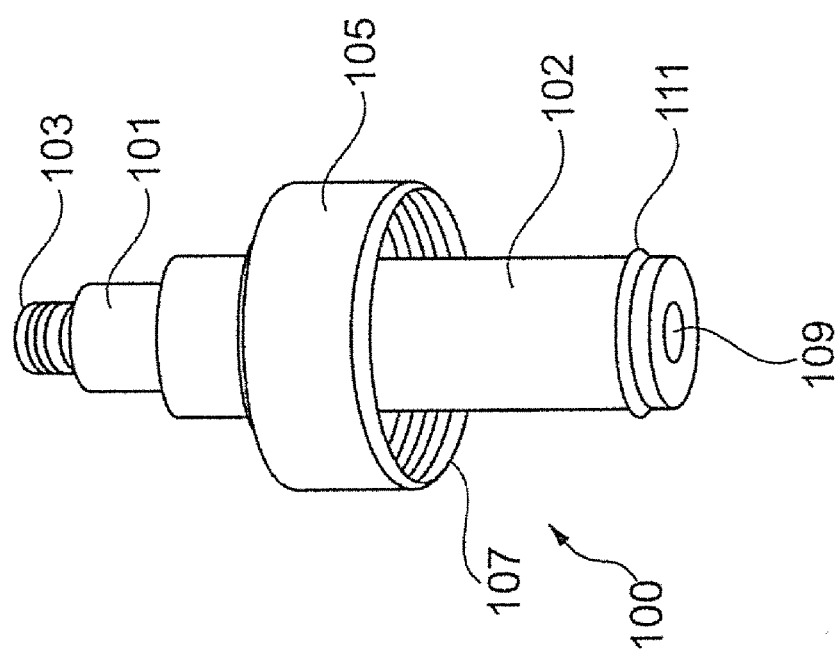
Figure 3:
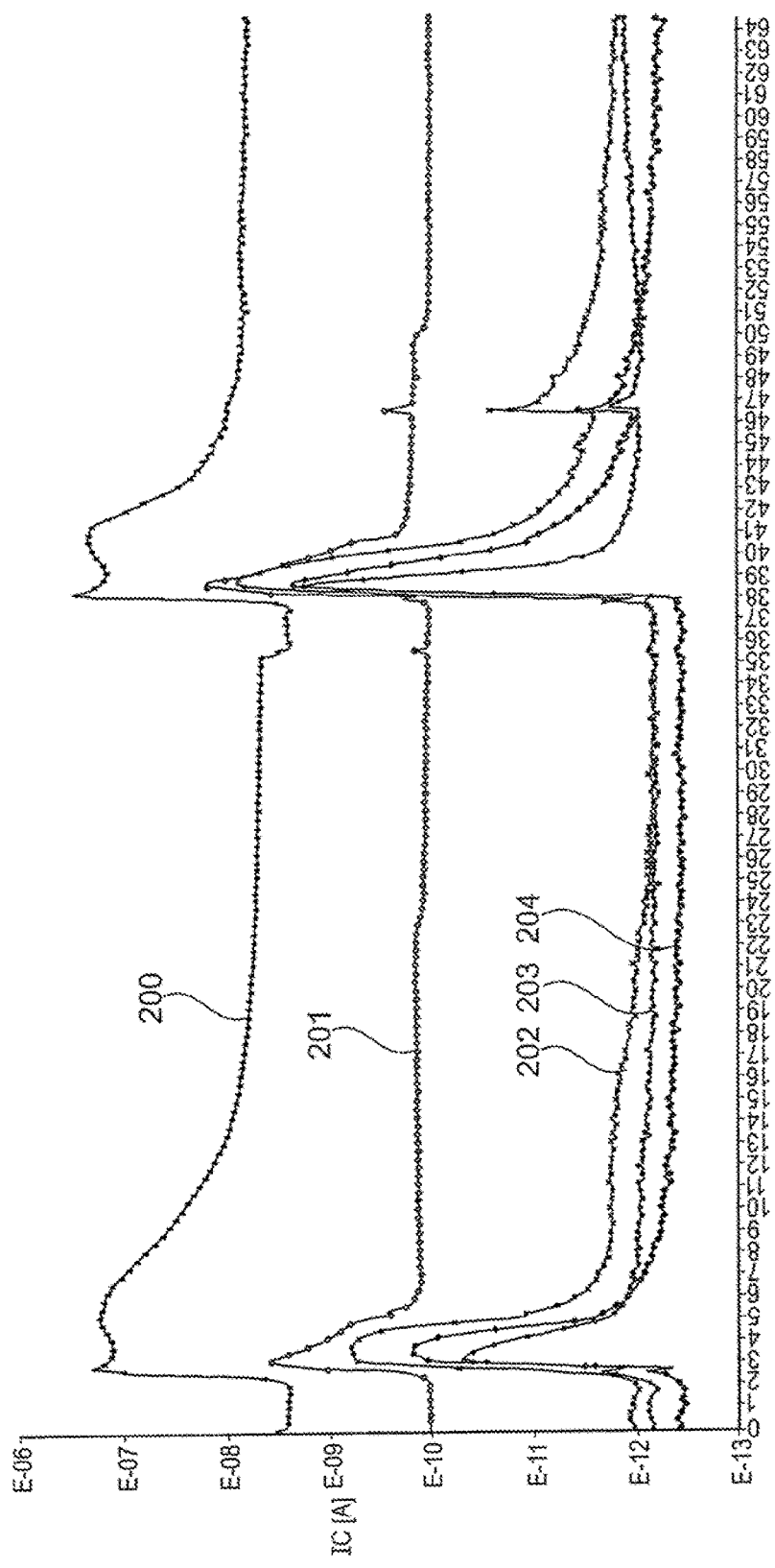
Figure 4:
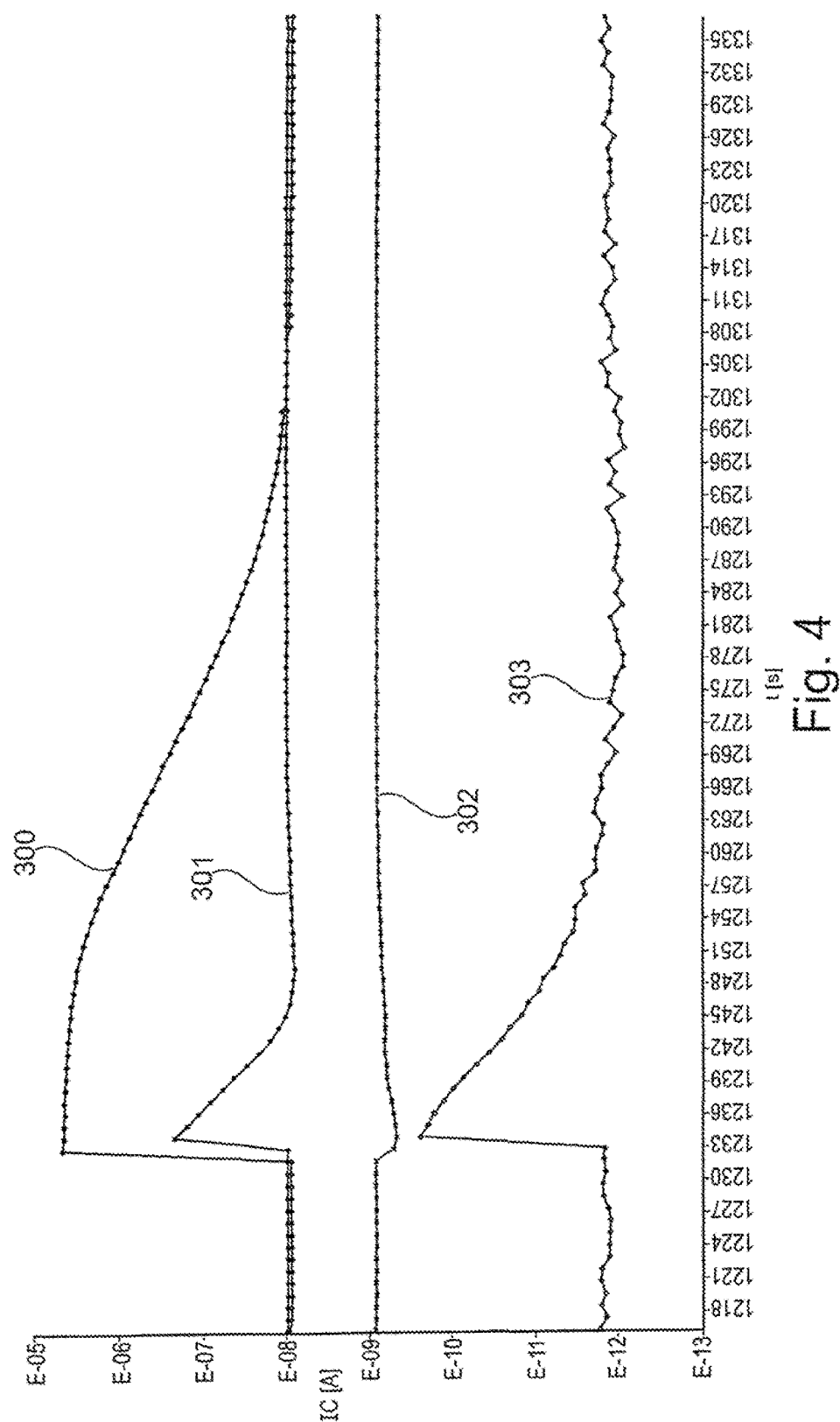
Figure 5:
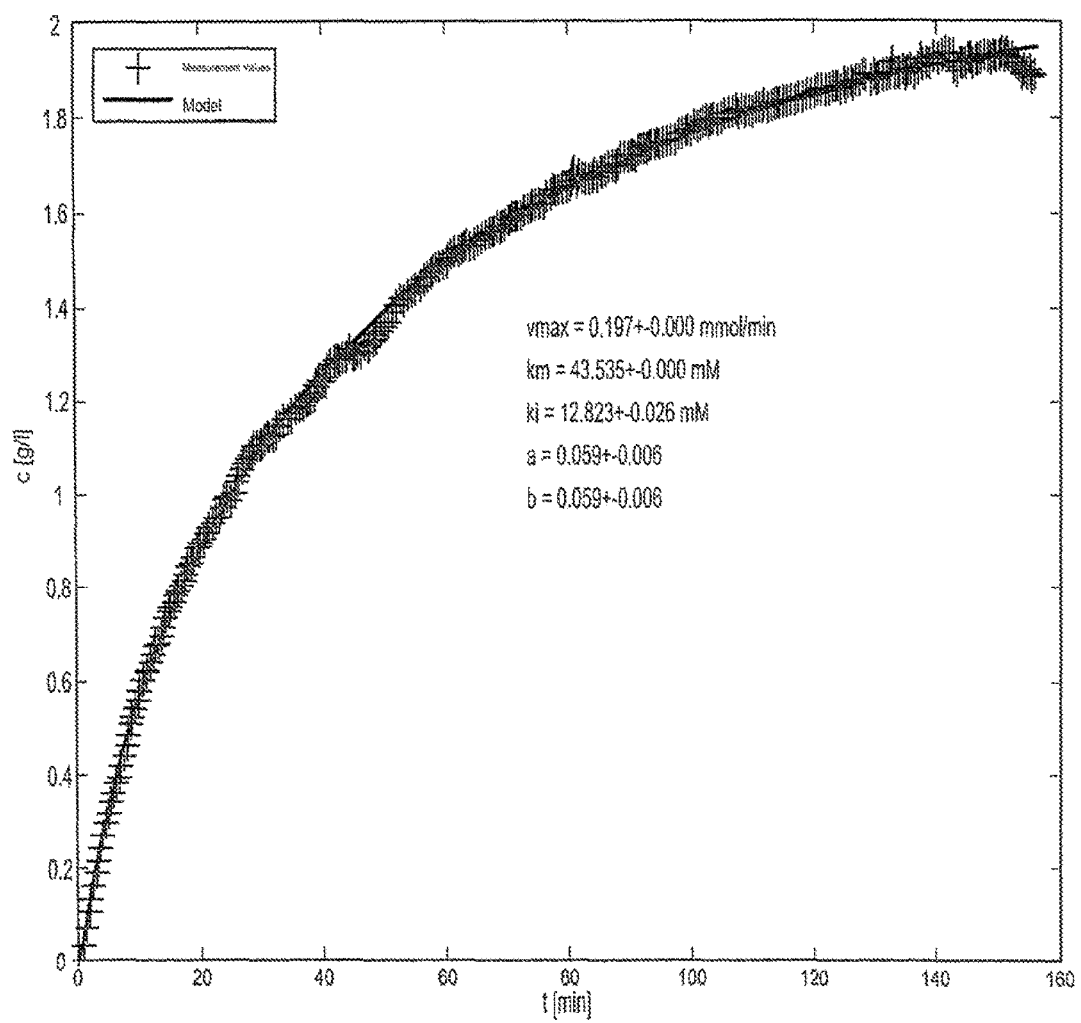
Figure 6:
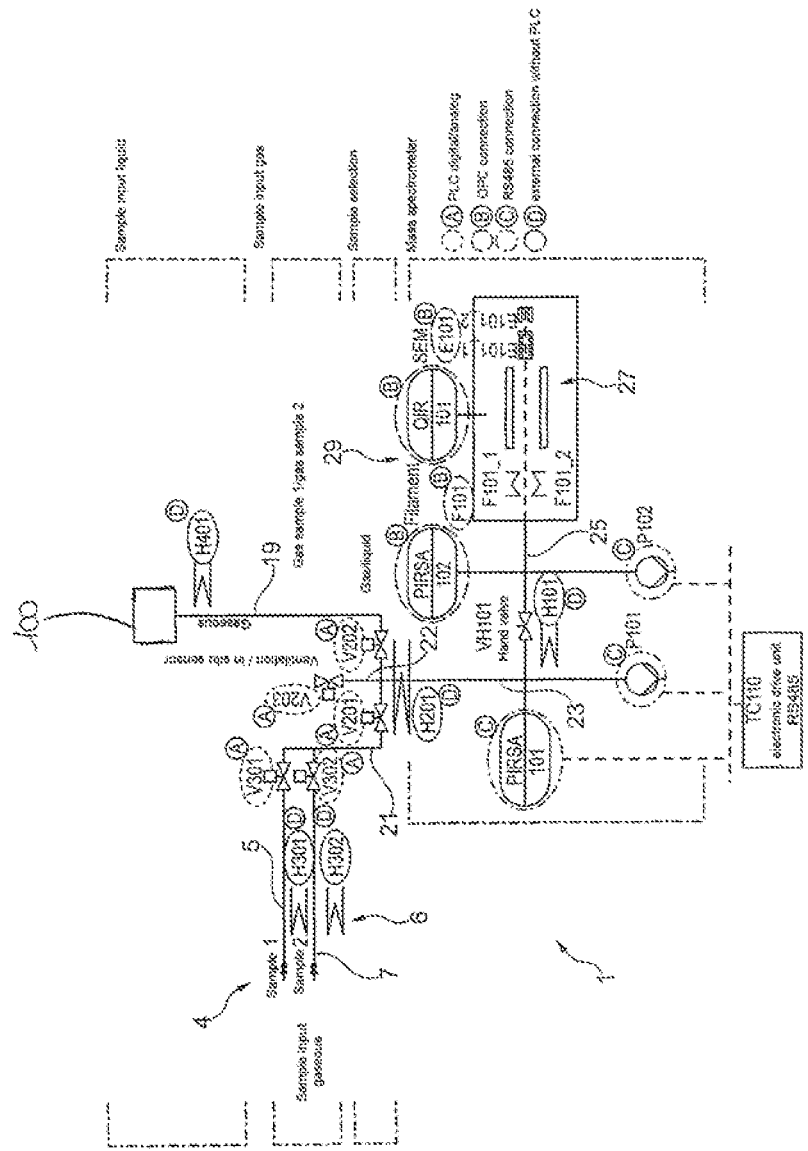

The figures show:

FIG. 1 a schematic representation of an apparatus preferred according to the invention, for analysis by mass spectrometer of both liquid and gaseous samples, FIG. 2 an in situ sensor according to the present invention, configured as an Ingold connector, FIG. 3 ion streams (IC) in [A] of different substances over time tin [min] in the incineration of a carbon fiber, FIG. 4 ion streams (IC) in [A] of different gases present in what is called a Reed switch, over time tin [s], FIG. 5 measured enzyme kinetics and mathematical modeling using a hyperbolic velocity equation, and FIG. 6 a schematic representation of an alternative apparatus that is preferred according to the invention, for analysis by gas spectrometer of both liquid and gaseous samples.

In particular, FIG. 1 shows an apparatus 1, in which a liquid sample can be introduced by way of an inlet 2 having a line 3, from a sample-taking space, and a gaseous sample can be introduced, in each instance, by way of inlets 4, 6 having lines 5 and 7. Alternatively or in addition, a calibration solution kept on hand in a container 9 can be introduced by way of an inlet 8 having a line 11. The liquid sample or the calibration solution is supplied to a membrane device M401 by means of a pump P401. The pump P401 is characterized by a flow rate of 0 to 50 milliliters per minute, preferably 10 milliliters per minute, and can thereby generate a system pressure of 0 to 400 bar. By way of a valve, preferably a pneumatic valve, V401, the liquid sample can optionally be passed to the membrane device M401, by way of the line 3, or the calibration solution can be passed to it by way of the line 11, by means of the pump P401, in liquid form. The liquid sample or the calibration solution flows past and parallel to a membrane 13 that is present in the membrane device M401. The membrane 13 is preferably a hydrophobic, at least partially porous membrane, by means of which volatile substances, which are present in the calibration solution or the liquid sample, can be converted to a gaseous aggregate state. The non-volatilized liquid component, or the component serving to wet the membrane 13, is either conducted away into a container 17 by way of a line 15, or returned to the sample-taking space by way of a line 16. This can be controlled with a valve, preferably a pneumatic valve, V402. The volatilized substances of the liquid sample or of the calibration solution are present in the gaseous state in a first flow element 19, preferably a line 19. The first flow element 19 can preferably be heated by means of a heating element H401. The lines 5 and 7 provided for the gaseous samples can also be heated by way of heating elements H301 and H302. The gaseous samples can optionally be introduced into a second flow element 21, preferably a line 21, by way of a valve, preferably a pneumatic valve, V301, or a valve, preferably a pneumatic valve, V302. A heating element is preferably also assigned to the second flow element 21. By means of a valve, preferably a pneumatic valve, V201, the substances present in the gaseous state can be introduced into a third flow element 23, by way of the flow element 21 or by means of a valve, preferably a pneumatic valve, V202, by way of the flow element 19. Introduction takes place, on the one hand, by means of corresponding switching and opening of the valves V201 and V202, and, on the other hand, additionally by means of the suction effect generated by a pump P101. By means of the pump P101, a pre-vacuum, which means that a pressure of 0.01 to 0.5 mbar is present, is particularly generated. A further flow element 22, which stands in fluid contact with the third flow element, can be used, on the one hand, as ventilation or for connection of an in situ sensor shown in FIG. 2. A valve, preferably a pneumatic valve, V203, closes the flow element 22 in one switching position, and produces a fluid connection to the outside or to the in situ sensor in another switching position. Furthermore, a PIRSA pressure meter PIRSA101 (P=pressure; I=indicator; R=recording; S=switchable; A=alarm) is assigned to the third flow element 23. By way of a hand valve VH101, the gaseous substances get from the third flow element 23 into a fourth flow element 25. The hand valve VH101 can also be configured as a valve that can be operated by way of a controller. A pump P102 is assigned to the fourth flow element 25, which pump is particularly suited for generating a high vacuum, in other words for production of a vacuum having a pressure of $10^{-5}$ mbar or less. Likewise, a PIRSA pressure meter PIRSA102 is assigned to this flow element 25. The PIRSA pressure meters PIRSA101 and PIRSA102 particularly serve to measure and record the pressure present in the third and fourth flow elements 23 and 25, and to trigger an alarm, if necessary, if the actual pressure differs from a preset reference pressure. A heating element H101 is assigned to the hand valve VH101. All the heating elements H101, H201, H301, H302, H401 particularly serve to prevent misting, in other words condensation or adsorption of the substances present in the gaseous state, on the corresponding flow elements. The gaseous substances present in the fourth flow element 25 subsequently reach a filament F101 present in a mass spectrometer 29, thereby causing the substances present in the gaseous state to be ionized. The ions produced are accelerated by means of a static, electric field, and fly centrally through four rod electrons that lie parallel, the intersection point of which, with a plane perpendicular to the cylinder axis, form a square, called the quadrupole 27. An m/e selection takes place in the alternating field between the quadrupole rods, so that in each instance, only particles having a defined mass can pass through the field. Subsequently, the ions impact in a detector E101 having a measurement amplifier, which detector measures the ion stream, which is converted to a count rate or to a partial pressure by the software of the connected PC. The detector E101 is a secondary electron multiplier E101_1 (abbreviated as SEM or SEV). Furthermore, it has a Faraday collector E101_2. The mass spectrometer 29 furthermore has a QIR sensor QIR101 (Q=quantity, I=indicator, R=recording). Furthermore, the pressure meter PIRSA101 and the pumps P101 and P102 are connected, in each instance, with an electronic drive unit, by way of an interface RS485.

The elements of the apparatus identified with the symbol A can be controlled using a digital or analog memory-programmable controller. The elements identified with a symbol B have an OPC connection. The elements identified with a symbol C have an RS485 interface connection, and the elements identified with the symbol D have an external connection, but no connection to the memory-programmed controller.

FIG. 2 shows an in situ sensor 100, which has a cylindrical inner part 101 with a non-visible outside thread, and a sleeve 102 with a non-visible inside thread, wherein the cylindrical inner part 101 is screwed into the sleeve 102, wherein the inside thread and the outside thread interact. The inner part 101 furthermore has a non-visible line, preferably a bore, which extends in the longitudinal direction, by means of which a fluid connection is present between the liquid medium or sample and the inlet of the apparatus for the liquid samples. Preferably, the in situ sensor 100 has a heating element, so that the entire sensor 100 can be heated. A membrane 109 is clamped in place using a suitable seal, preferably an O-ring seal, between the inner part 101 and the sleeve 102, preferably by means of tightening the sleeve 102. The sleeve 102 has an opening, preferably a bore, at this membrane end, so that the liquid sample can wet the membrane with a sufficient amount, when used as intended. This membrane 109 is preferably inserted into the in situ sensor 100 in such a manner that a curvature, preferably a slight curvature to the outside, in other words in the direction of the liquid or sample, occurs. By means of this preferred curvature, the volatilization of the volatile substances present in the medium is improved, and/or the biofilm formation on the membrane in a fermenter is reduced. To prevent biofilm formation, a wiping element is preferably provided, alternatively or in addition. Preferably, this membrane 109 is supported by means of a non-visible disk, preferably a sintered disk, preferably counter to the curvature. By means of a cap nut 105, which is also present and has a thread 107, the in situ sensor can preferably be attached to a reaction vessel, preferably to a fermenter, and preferably ends flush with the reactor interior, preferably fermenter interior, preferably in fluid-tight manner, by way of a ring seal 111 that lies against the sleeve 102 on the outside. An outside thread 103 is present at the end of the sensor 100 that lies opposite the membrane end, with which thread the in situ sensor 100 can be connected with the apparatus 1, particularly with the flow element 19, preferably directly.

FIG. 3 shows ion streams (IC) in [A] over time tin [min] during incineration of a carbon fiber at 700° C. In this regard, the curve 200 shows the ion stream of $CO_2$, the curve 201 shows the ion stream of hydrogen, the curve 202 that of benzene, the curve 203 that of aliphatic hydrocarbons, and the curve 204 that of aromatic hydrocarbons.

FIG. 4 shows the ion streams (IC in [A]) over time tin [s] of different gases present in a Reed switch (nitrogen (curve 300), hydrogen (curve 301), oxygen (curve 302), and helium (curve 303)). For online measurement of the gas composition of the glass tube of the Reed switch, the tube was broken in situ, using a magnet, directly under vacuum.

FIG. 5 shows the methanol concentration in the enzymatic production of methanol and formic acid from formaldehyde. By means of a calibration of the mass spectrometer, which was carried out beforehand, conversion of the ion streams to concentrations is possible. Because of the great data density of the kinetics, mathematical modeling of the enzyme reaction is possible. Accordingly, FIG. 5 shows the methanol concentration c in g/L over time t in minutes, as it progresses.

FIG. 6 shows an alternative apparatus 1, which corresponds to the apparatus shown in FIG. 1, wherein, however, an in situ sensor 100, introduced into a bioreactor, not shown, represents the inlet for a liquid sample into the first flow element 19. The volatile substances from the liquid sample, which are to be analyzed, are converted to the gaseous state at the in situ sensor 100, and introduced into the first flow element 19.

The invention claimed is:
1. A method for analyzing substances present in liquid and gaseous samples by mass spectrometry, the method comprising:
   a) introducing either or both of: i) at least one first substance in a liquid sample into a first flow element of an apparatus and volatilizing the liquid sample on or in a membrane within the apparatus that is not permeable to liquids but is gas permeable such that the at least one first substance is present in a gaseous state, or ii) at least one second substance in a gaseous sample such that the at least one second substance is present in a gaseous state, into a second flow element of the apparatus, wherein the first flow element is different from the second flow element, so that at least one of the at least one first substance or the at least one second substance is present in a gaseous state in the apparatus;
   a1) comprising introducing the at least one of the at least one first substance or the at least one second substance present in the gaseous state in step a) into a third flow element of the apparatus, where a pressure of 0.01 to 0.5 mbar is present in the third flow element:
   introducing the at least one of the at least one first substance or the at least one second substance present in the gaseous state in step a) into a fourth flow element of the apparatus, when a pressure of $10^{-5}$ mbar or less is present in the fourth flow element, and wherein when a pressure increase is detected in the fourth flow element, the method further comprises closing a controllable valve device disposed between the third and fourth flow element, so that there is no fluid contact between the third and fourth flow element; and
   b) analyzing the at least one of the at least one first substance or the at least one second substance in the gaseous state that is present in step a) using a mass spectrometer of the apparatus.

2. The method according to claim 1, wherein the analyzing according to step b) comprises the following steps:
   i) ionizing the at least one of the at least one first substance or the at least one second substance present in the gaseous state,
   ii) accelerating the at least one substance ionized in step i),
   iii) selecting the at least one substance accelerated in step ii), and
   iv) detecting the at least one substance selected in step iii).

3. The method according to claim 1, wherein at least one of the first, second, third and fourth flow elements is heated to a temperature of 60 to 80° C.

4. The method according to claim 1, wherein the introducing either the at least one first substance in the liquid sample into the first flow element or the at least one second substance in the gaseous sample into second flow element is controlled in such a manner that in step a1) and/or a2), equal amounts of the at least one of the at least one first substance or the at least one second substance of step a) are present in the third flow element when the liquid sample and the gaseous sample are both introduced in step a).

5. The method according to claim 1, wherein non-volatile substances in the liquid sample are determined by means of a detector for determination of non-volatile substances in liquid samples.

6. The method according to claim 1, comprising introducing both the at least one first substance in the liquid sample into the first flow element and the at least one second substance in the gaseous sample into the second flow element, wherein the at least one first substance and the at least one second substance are the same.

7. The method according to claim 1, comprising introducing both the at least one first substance in the liquid sample into the first flow element and the at least one second substance in the gaseous sample into the second flow element, wherein the at least one first substance and the at least one second substance are different.

8. A method for analyzing substances present in liquid and gaseous samples by mass spectrometry, the method comprising:
   a) introducing either or both of: i) at least one first substance of a liquid sample into a first flow element of an apparatus or ii) at least one second substance of a gaseous sample into a second flow element of the apparatus, wherein the first flow element is different from the second flow element, so that at least one of the at least one first substance or the at least one second substance is present in a gaseous state in the apparatus;
   a1) introducing the at least one of the at least one first substance or the at least one second substance present in the gaseous state in step a) into a third flow element of the apparatus, wherein a pressure of 0.01 to 0.5 mbar is present in the third flow element;
   a2) introducing the at least one of the at least one first substance or the at least one second substance present in the gaseous state in step a1) into a fourth flow element of the apparatus; and
   b) analyzing the at least one of the at least one first substance or the at least one second substance in the gaseous state that is present in step a) by using a mass spectrometer,
   wherein when a pressure increase is detected in the fourth flow element, the method further comprises closing a controllable valve device disposed between the third and fourth flow element, so that there is no fluid contact between the third and fourth flow element.

9. The method according to claim 8, wherein in step a2) a pressure of $10^{-5}$ mbar or less is present in the fourth flow element.

* * * * *